(12) United States Patent
Yadin

(10) Patent No.: US 7,344,557 B2
(45) Date of Patent: Mar. 18, 2008

(54) CATHETER BALLOON SYSTEMS AND METHODS

(75) Inventor: Amnon Yadin, Pleasanton, CA (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 302 days.

(21) Appl. No.: 10/985,005

(22) Filed: Nov. 10, 2004

(65) Prior Publication Data

US 2005/0102019 A1 May 12, 2005

Related U.S. Application Data

(60) Provisional application No. 60/548,868, filed on Mar. 2, 2004, provisional application No. 60/547,778, filed on Feb. 27, 2004, provisional application No. 60/518,870, filed on Nov. 12, 2003.

(51) Int. Cl.
*A61F 2/06* (2006.01)
*A61M 29/02* (2006.01)

(52) U.S. Cl. ............... 623/1.11; 623/1.35; 604/103.06; 604/103.07; 604/103.08; 604/103.14

(58) Field of Classification Search ............... 623/1.11, 623/1.27, 1.28, 1.35, 1.29; 604/103.01, 103.05, 604/103.14, 103.06, 103.07, 103.08
See application file for complete search history.

(56) References Cited

U.S. PATENT DOCUMENTS

| 1,596,754 | A | 8/1926 | Moschelle |
| 3,657,744 | A | 4/1972 | Ersek |
| 3,872,893 | A | 3/1975 | Roberts |
| 4,140,126 | A | 2/1979 | Choudhury |
| 4,309,994 | A | 1/1982 | Grunwald |
| 4,410,476 | A | 10/1983 | Redding et al. |
| 4,413,989 | A | 11/1983 | Schjeldahl |
| 4,421,810 | A | 12/1983 | Rasmussen |
| 4,453,545 | A | 6/1984 | Inoue |
| 4,479,497 | A | * | 10/1984 | Fogarty et al. ............. 606/194 |
| 4,503,569 | A | 3/1985 | Dotter |
| 4,552,554 | A | 11/1985 | Gould et al. |

(Continued)

FOREIGN PATENT DOCUMENTS

CA  2318314  7/1999

(Continued)

OTHER PUBLICATIONS

Serruys et al., *The New England Journal of Medicine*, vol. 331, No. 8, pp. 489-495 (1994).

(Continued)

*Primary Examiner*—Glenn K. Dawson
*Assistant Examiner*—Kathleen Sonnett
(74) *Attorney, Agent, or Firm*—Merchant & Gould P.C.

(57) ABSTRACT

Apparatus and method are provided for treatment of a bifurcation of a body lumen. The apparatus includes an elongated catheter body having a proximal end and a distal end. A balloon is associated with the distal end of the balloon catheter. The balloon includes a main vessel balloon for treating a main vessel of the bifurcation, and a branch vessel balloon for treating a branch vessel of the bifurcation. The branch vessel balloon includes an accordion configuration capable of being expanded from an unexpanded collapsed accordion configuration to an expanded accordion configuration extending into the branch vessel.

3 Claims, 15 Drawing Sheets

U.S. PATENT DOCUMENTS

| | | |
|---|---|---|
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,334,153 A * | 8/1994 | McIntyre et al. ........ 604/99.02 |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Ansel |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jiminez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |

| Patent No. | Date | Inventor(s) |
|---|---|---|
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,797,947 A * | 8/1998 | Mollenauer ............... 606/192 |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Juin Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,090,133 A * | 7/2000 | Richter et al. ............. 623/1.35 |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,203,569 B1 | 3/2001 | Wijay |
| 6,210,380 B1 | 4/2001 | Mauch |
| 6,210,429 B1 | 4/2001 | Vardi |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Her et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,358,266 B1 * | 3/2002 | Bonutti ..................... 606/190 |
| 6,361,544 B1 | 3/2002 | Wilson et al. |
| 6,361,555 B1 | 3/2002 | Wilson |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,478,816 B1 | 11/2002 | Kveen et al. |
| 6,482,211 B1 | 11/2002 | Choi |

| | | |
|---|---|---|
| 6,485,511 B2 | 11/2002 | Lau et al. |
| 6,494,905 B1 | 12/2002 | Zedler et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,022 B2 | 7/2003 | Lau et al. |
| 6,599,316 B2 | 7/2003 | Vardi et al. |
| 6,645,241 B1 | 11/2003 | Strecker |
| 6,689,156 B1 | 2/2004 | Davidson et al. |
| 6,692,483 B2 | 2/2004 | Vardi et al. |
| 6,706,062 B2 | 3/2004 | Vardi et al. |
| 6,835,203 B1 | 12/2004 | Vardi et al. |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037140 A1* | 11/2001 | Gaudoin et al. ........... 623/1.11 |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0041927 A1 | 11/2001 | Solem |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Bockstegers et al. |
| 2002/0035392 A1 | 3/2002 | Wilson |
| 2002/0042650 A1 | 4/2002 | Vardi et al. |
| 2002/0052648 A1 | 5/2002 | McGuckin et al. |
| 2002/0058990 A1 | 5/2002 | Jang |
| 2002/0072790 A1 | 6/2002 | McGuckin et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1* | 10/2002 | Vardi et al. ................ 623/1.11 |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1* | 12/2002 | Callol et al. ................ 606/108 |
| 2002/0193872 A1 | 12/2002 | Trout et al. |
| 2002/0193873 A1* | 12/2002 | Brucker et al. ............ 623/1.35 |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0050688 A1 | 3/2003 | Fischell et al. |
| 2003/0055378 A1* | 3/2003 | Wang et al. ........... 604/103.07 |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon et al. |
| 2003/0125802 A1 | 7/2003 | Callol et al. |
| 2004/0015227 A1 | 1/2004 | Vardi et al. |
| 2004/0049259 A1 | 3/2004 | Strecker |
| 2004/0072849 A1 | 4/2004 | Scheiber et al. |
| 2004/0117003 A1 | 6/2004 | Ouriel et al. |
| 2004/0133268 A1 | 7/2004 | Davidson et al. |
| 2004/0138737 A1 | 7/2004 | Davidson et al. |
| 2004/0148006 A1 | 7/2004 | Davidson et al. |
| 2005/0060027 A1* | 3/2005 | Khenansho et al. ....... 623/1.35 |

FOREIGN PATENT DOCUMENTS

| | | |
|---|---|---|
| DE | 9014845.2 | 2/1991 |
| DE | 29701758 | 5/1997 |
| EP | 551179 | 7/1993 |
| EP | 684022 | 11/1995 |
| EP | 804907 | 5/1997 |
| EP | 876805 | 11/1998 |
| EP | 884028 | 12/1998 |
| EP | 891751 | 1/1999 |
| EP | 897698 | 2/1999 |
| EP | 897700 | 2/1999 |
| EP | 904745 | 3/1999 |
| EP | 1031328 | 8/2000 |
| EP | 1031330 | 8/2000 |
| EP | 1157674 | 11/2001 |
| EP | 646365 | 1/2004 |
| FR | 2678508 | 1/1993 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | WO 96/29955 | 10/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/15103 | 4/1999 |
| WO | WO 99/17680 | 4/1999 |
| WO | WO 99/34749 | 7/1999 |
| WO | WO 99/36002 | 7/1999 |
| WO | WO 99/39661 | 8/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |

| | | |
|---|---|---|
| WO | WO 2004/026180 A2 | 4/2004 |
| WO | WO 2005/046757 A2 | 5/2005 |
| WO | WO 2005/122958 A1 | 12/2005 |

OTHER PUBLICATIONS

Fischmann et al., *The New England Journal of Medicine*, vol. 331, No. 8, pp. 496-501 (1994).

Nakamura et al., *Catheterization & Cardiovascular Diagnosis* 34-353-361 (1995).

Caputo et al., *The American Journal of Cardiology*, vol. 7, pp. 1226-1230 (1996).

Colombo et al., *Catheterization and Cardiovascular Diagnosis*, vol. 30, pp. 327-330 (1993).

Carrie et al., *Catheterization and Cardiovascular Diagnosis*, vol. 37, pp. 311-313 (1996).

Katoh et al., *Catheterization and Cardiovascular Diagnosis*, vol. 40, pp. 400-402 (1997).

Lewis et al., *American Heart Journal*, vol. 127, pp. 1600-1607 (1994).

Dichek, D.A. et al.; *Circulation*, 80: 1347-1353 (1989).

Chevalier, B. et al.; *American Journal of Cardiology*, 82: 943-949 (1998).

Yamashita, T. et al.; *Journal of American College of Cardiology*, 35: 1145-1151 (2000).

Satler, S., et al.; *Catheterization and Cardiovascular Interventions*, 50: 411-412 (2000).

* cited by examiner

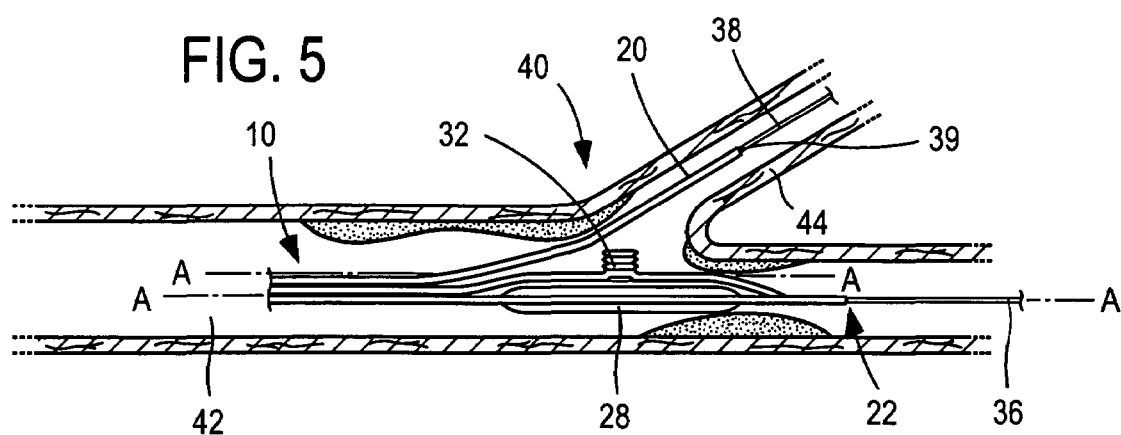
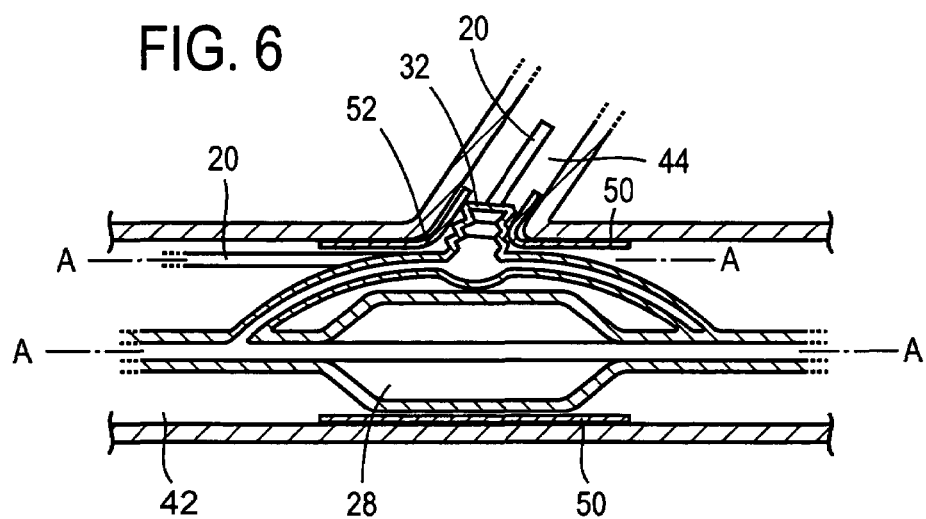

CATHETER BALLOON SYSTEMS AND METHODS

CROSS REFERENCE TO RELATED APPLICATIONS

This application claims the benefit of priority of U.S. Provisional Application No. 60/518,870, filed Nov. 12, 2003, entitled "STENT DELIVERY SYSTEMS"; U.S. Provisional Application No. 60/547,778, filed Feb. 27, 2004, entitled "SIDE BALLOON STENT DELIVERY SYSTEMS"; U.S. Provisional Application No. 60/548,868, filed Mar. 2, 2004, entitled "STENT DELIVERY SYSTEMS," the disclosures of which are hereby incorporated herein by reference.

This application is related to co-pending U.S. patent application Ser. No. 10/705,247, filed Nov. 12, 2003, U.S. patent application Ser. No. 10/802,036, filed Mar. 17, 2004, U.S. patent application Ser. No. 10/834,066, filed Apr. 29, 2004; and U.S. patent application Ser. No. 10/893,278, filed Jul. 19, 2004. The complete disclosures of the above-referenced applications are incorporated herein by reference.

FIELD OF THE INVENTION

The present invention relates to the field of medical balloon catheters and, more particularly, to systems for delivering a stent at or near a bifurcation of a body lumen.

BACKGROUND OF THE INVENTION

Balloon catheters, with or without stents, are used to treat strictures, stenoses, or narrowings in various parts of the human body. Devices of numerous designs have been utilized for angioplasty, stents and grafts or combination stent/grafts. Varied catheter designs have been developed for the dilatation of stenoses and to deliver prostheses to treatment sites within the body lumen.

Illustrative procedures involving balloon catheters include percutaneous transluminal angioplasty (PTA) and percutaneous transluminal coronary angioplasty (PTCA), which may be used to reduce arterial build-up such as caused by the accumulation of atherosclerotic plaque. These procedures involve passing a balloon catheter over a guidewire to a stenosis with the aid of a guide catheter. The guidewire extends from a remote incision to the site of the stenosis, and typically across the lesion. The balloon catheter is passed over the guidewire, and ultimately positioned across the lesion.

Once the balloon catheter is positioned appropriately across the lesion, (e.g., under fluoroscopic guidance), the balloon is inflated, which breaks the plaque of the stenosis and causes the arterial cross section to increase. Then the balloon is deflated and withdrawn over the guidewire into the guide catheter, and from the body of the patient.

In many cases, a stent or other prosthesis must be implanted to provide support for the artery. When such a device is to be implanted, a balloon catheter which carries a stent on its balloon is deployed at the site of the stenosis. The balloon and accompanying prosthesis are positioned at the location of the stenosis, and the balloon is inflated to circumferentially expand and thereby implant the prosthesis. Thereafter, the balloon is deflated and the catheter and the guidewire are withdrawn from the patient.

Administering PTCA and/or implanting a stent at a bifurcation in a body lumen poses further challenges for the effective treatment of stenoses in the lumen. For example, dilating a main vessel at a bifurcation may cause narrowing of the adjacent branch vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing. However, simultaneously deploying multiple and/or bifurcated balloons with or without endoluminal prostheses, hereinafter individually and collectively referred to as a bifurcated assembly, requires accurate placement of the assembly. Deploying multiple stents requires positioning a main body within the main vessel adjacent the bifurcation, and then attempting to position another stent separately into the branch vessel of the body lumen. Alternatives to that include deploying a dedicated bifurcated stent including a tubular body or trunk and two tubular legs extending from the trunk. Some examples include U.S. Pat. No. 5,723,004 to Dereume et al., U.S. Pat. No. 4,994,071 to MacGregor, and U.S. Pat. No. 5,755,734 to Richter et al.

Additional bifurcation stent delivery systems that provide improved reliable treatment at bifurcations are disclosed, for example, in U.S. Pat. No. 6,325,826 to Vardi et al. and U.S. Pat. No. 6,210,429 to Vardi et al. The contents of the '826 and '429 patents aforementioned patents are incorporated herein by reference.

A need still exists for further improved devices and techniques for treating a bifurcated body lumen. For example, a need further exists for additional stent delivery systems that can be used with stents having a branch access side hole and/or an extendible branch portion.

SUMMARY OF THE INVENTION

The present invention is directed to devices and techniques for treating a bifurcated body lumen including systems for delivering an endoluminal prosthesis at or near a bifurcation of a body lumen. Systems, devices and techniques are disclosed comprising balloon catheters configured to successfully and reliably deploy stents at a bifurcation in a body lumen. Additionally, the balloon catheters can be employed as balloon angioplasty catheters to treat occlusions in blood vessels such as for instance in percutaneous transluminal coronary angioplasty (PTCA) procedures.

According to one aspect, the present invention provides a catheter assembly for use in bifurcated vessels. The assembly includes an elongated catheter body having a proximal end and a distal end and a balloon associated with the distal end of the balloon catheter. The balloon includes a main vessel balloon for treating a main vessel of the bifurcation, and a branch vessel balloon for treating a branch vessel of the bifurcation. The branch vessel balloon includes an accordion configuration capable of being expanded from an unexpanded collapsed accordion configuration to an expanded accordion configuration extending into the branch vessel.

According to another aspect, the branch vessel balloon includes accordion folds and the folds are substantially collapsed against each other in the unexpanded configuration, and separated from each other in the expanded configuration.

In another aspect, the catheter assembly includes a bifurcated stent, which is disposed on the balloon. In particular, the present invention provides a catheter assembly including a bifurcated stent, which has a main vessel portion and an extendible branch vessel portion. The branch vessel balloon is disposed substantially adjacent the extendible branch portion. Upon expansion, the branch vessel balloon expands the extendible branch vessel portion of the stent into the branch vessel.

In another aspect of the invention, the catheter includes an inflation lumen, and the balloon has an interior in fluid communication with the inflation lumen. More particularly, the inflation lumen comprises two inflation lumens. The first inflation lumen is in fluid communication with the interior of the branch vessel balloon. The second inflation lumen is in communication with an interior of the main vessel balloon.

In another aspect of the invention, the branch and main vessel balloons described above comprise a unitary balloon, and in other embodiments, the branch vessel balloon is separate from the main vessel balloon.

According to another aspect, the present invention provides a catheter assembly, which includes a side sheath associated with the elongated catheter body. At least a portion of the side sheath extends along the distal end of the catheter body and adjacent the branch vessel balloon. In some aspects of the invention, the branch vessel balloon is disposed on the side sheath. In another aspect of the invention, the side sheath is disposable in the branch vessel. Additionally, the main vessel balloon is disposable in the main vessel during placement of the catheter assembly in a bifurcated vessel. The accordion configuration can be oriented to expand in a direction substantially perpendicular to a longitudinal axis of the main vessel balloon. In a further aspect of the invention, the branch vessel balloon is located on the side sheath and oriented to expand in a direction substantially parallel to a longitudinal axis of the side sheath.

In another aspect, the branch vessel balloon comprises a herniation on the main vessel balloon, and in another aspect, the present invention provides a catheter assembly which includes a side sheath. One end of the branch vessel balloon is slidably affixed to the side sheath.

According to an additional aspect, the profile of the accordion folds of the catheter assembly of the present invention is substantially either round, elliptical, square, hexagonal or octagonal when viewed along the direction of inflation. Additionally, in other aspects, the profile of the accordion folds is substantially triangular or round when viewed perpendicularly to the direction of inflation.

In a further aspect of the invention, the accordion configuration includes a plurality of fluidly connected cells connected in series. The series defines an axis of primary inflation. In another embodiment, the successive cells have a different size from the preceding cells in the series. In a further aspect, the cells are adapted to merge into a substantially tubular structure when fully expanded.

According to yet another aspect, the present invention provides a catheter assembly for use in bifurcated vessels. The assembly includes an elongated catheter body having a proximal end and a distal end and a balloon associated with the distal end of the balloon catheter. The balloon includes a main vessel balloon for treating a main vessel of the bifurcation and a branch vessel balloon for treating a branch vessel of the bifurcation. The branch vessel balloon comprises a plurality of fluidly connected cells connected in series, the series defining an axis of primary inflation. When the branch vessel balloon is expanded, expansion along the axis of primary inflation is greater than expansion in a radial direction, which is substantially perpendicular to the axis of primary inflation.

A further aspect of the present invention provides a catheter assembly having successive cells, which differ in size from the preceding cells in the series. In another aspect, the cells are adapted to merge into a substantially tubular structure when fully expanded.

According to another aspect, the present invention provides a method of treating a bifurcation of a body lumen. The bifurcation includes a main vessel and a branch vessel. The method includes introducing a balloon and stent assembly into the main vessel, the balloon having at least one accordion inflation portion, wherein the accordion inflation portion comprises a plurality of accordion folds; positioning the assembly at the bifurcation; and inflating the balloon to expand the stent in the main vessel.

A further aspect of the invention provides a method of treating a bifurcation of a body lumen in which the step of inflating includes expanding a portion of the stent outwardly toward the branch vessel. Another aspect provides a method in which the accordion configuration expands the portion of the stent outwardly toward the branch vessel. The body lumen described above can be a blood vessel.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention.

FIG. 5 is a view of the stent delivery system of FIG. 1 in a blood vessel located at a bifurcation in the vessel without a stent mounted thereon in accordance with a method of the present invention.

FIG. 6 is a cross-sectional side view of the stent delivery system of FIG. 1 with a stent mounted thereon and shown in the expanded condition.

DESCRIPTION OF THE PREFERRED EMBODIMENTS

Figure 1:
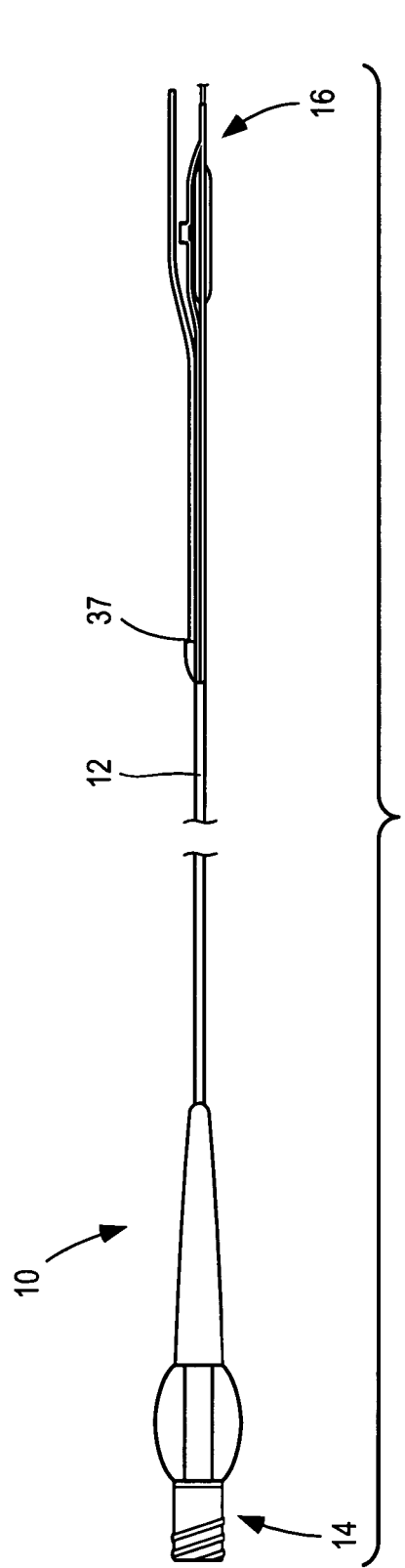
FIG. 1 is a side view of an illustrative embodiment of a stent delivery system constructed in accordance with the present invention.

The present invention relates to balloon catheters such as balloon angioplasty catheters to treat occlusions in blood vessels. The balloon catheters can be used alone or with a stent, prosthesis or graft. Such a stent delivery system can be used for placement of a stent in a body lumen, particularly at vessel bifurcations. A preferred stent to be delivered is generally configured to at least partially cover a portion of a branch vessel as well as a main vessel. In general, a wide variety of stents and deployment methods may be used with the stent delivery system embodiments of the present invention and the present invention should be understood to not be limited to any particular stent design or configuration. Examples of the types of stents that may be used with the delivery systems of the present invention are disclosed, for example, in U.S. Pat. No. 6,210,429 to Vardi et al., U.S. Pat. No. 6,325,826 to Vardi et al., and U.S. Patent Publication No. US2004-0138737, entitled "Stent With a Protruding Branch Portion For Bifurcated Vessels," and U.S. Publication No. US2004-0212940, entitled "Stent With Protruding Branch Portion for Bifurcated Vessels," the entire contents of which are incorporated herein by reference. In general, the aforementioned stent includes a branch portion located at some point along the length of the stent that is configured to be extendible into a branch vessel in a vessel bifurcation. Once the stent is in position in the main vessel and the branch portion is aligned with the side branch vessel the stent can be expanded and the delivery system in accordance with the principles of the invention is particularly adapted to expand the stent branch portion into the side branch vessel. The stent, including the branch portion, may be expanded with a single expansion or multiple expansions.

The balloon catheter system and stent delivery system and methods of use in accordance with the principles of the invention are directed to a type that treats bifurcations in the vasculature, for example, where a branch vessel extends from a main vessel. The system provides for the branch balloon to extend into the branch vessel and, preferably, deploy an extendible branch portion of a stent into the branch vessel as disclosed in the patents and applications discussed above, for example. Embodiments of the systems and methods are discussed more fully herein. In general, however, in accordance with the principles of the invention, balloon expansion into the branch vessel and, more particularly, to expand the branch stent structure into the branch vessel, can be accomplished by way of an accordion balloon as described and illustrated herein. The accordion balloon is constructed to be expandable, predominantly axially, e.g., along its axis of primary inflation, allowing it to extend into the branch vessel and/or deploy the extendible branch structure of the above-described stent.

In accordance with the principles of the invention, embodiments of the accordion balloon are shown and described herein. In certain embodiments, the accordion balloon can be associated or integral with the side sheath catheter. Alternatively the accordion balloon can be associated or integral with the main balloon catheter as described in more detail in the following. Additionally, in certain embodiments (see, e.g., FIGS. 11-17) the accordion balloon can be slidably attached to the catheter or sheath to accommodate the axial or longitudinal expansion of the accordion balloon.

Figure 2:
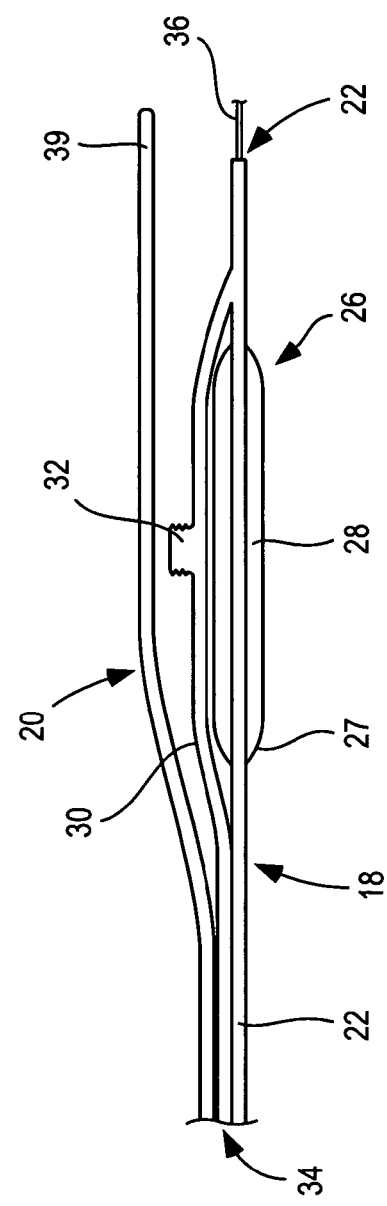
FIG. 2 is an enlarged side view taken of the distal portion of the system of FIG. 1.

An illustrative view of one embodiment of a stent delivery system 10 constructed in accordance with the present invention is shown in FIG. 1. Stent delivery system 10 generally comprises an elongate main catheter shaft 12 extending from a proximal end 14 to a distal end 16. As best seen in FIG. 2, distal end 16 has a bifurcated tip structure with two branch portions, a main vessel branch portion 18 and a side branch sheath 20 that branches off of main catheter shaft 12.

Balloon 26 generally includes an inflatable portion 32 comprising an accordion balloon, as discussed in more detail in the following. Balloon 26 as shown can be a bifurcated balloon, which is attached to main vessel branch portion 18 adjacent the distal end 16 and comprises first and second branch portions 27, 30. First branch portion 27 of balloon 26 comprises an elongate inflatable portion 28. Second branch portion 30 of balloon 26 comprises the second inflatable portion or auxiliary inflatable portion 32 comprising the accordion balloon. Second branch portion 30 includes an inflation lumen that branches off from first branch portion 27 proximally from the balloon 26 and extends substantially adjacent elongate inflatable portion 28. The distal end of second branch portion 30 is attached to first branch portion 27 at a location distally from the balloon 26. In one preferred embodiment, the distal end of branch portion 30 is fixedly attached distally of balloon 26 in order to prevent at least the second inflatable portion 32 from moving around the first branch portion 27, although in alternate embodiments it may be removably attached.

In a preferred embodiment, first inflatable portion 28 is generally cylindrical and extends coaxially along main vessel branch portion 18. Second inflatable portion 32 may have an accordion shape and size adapted to extend into the branch vessel as shown and described herein. For example, portion 32 may have a generally offset configuration and may be positioned adjacent or in abutting relation with respect to elongate inflatable portion 28.

The first and second inflatable portions can have varied shapes, sizes and positioning in accordance with the principles of the invention. For example, in alternative design variations, accurate sizing and positioning of the inflatable portions relative to the vessel may be achieved.

According to the present invention, the inflatable portions, or balloons, can be constructed of any suitable material. Preferably, they are made of non-compliant materials. The balloons may be constructed of an appropriate polymeric material. Particular examples include the polyamide family, or the polyamide blend family, polyethylene (PE), polyethylene terephthalate (PET), polyurethanes, polyamides, and polyamide blends such as PBAX. The compliance of the first inflatable portion 28 and the second inflatable portion 32 can be the same or different. In one preferred embodiment, second inflatable portion 32 is longitudinally positioned at a generally central location relative to the first inflatable portion 28. In alternate embodiments, second inflatable portion 32 may be positioned at any position adjacent first inflatable portion 28.

In a preferred embodiment, balloon branch portions 27 and 30 have a common inflation lumen 34. Inflation lumen 34 can be conventional, and extend from a portion of the stent delivery system which always remains outside of the patient (not pictured). Inflation lumen 34 extends distally into each of first and second branch portions 27 and 30 and thus, inflation lumen 34 is in fluid communication with the interiors of first inflatable portion 28 and second inflatable portion 32. Thus inflation lumen 34 is used to supply pressurized inflation fluid to first inflatable portion 28 and second inflatable portion 32 when it is desired to inflate balloon 26. Inflation lumen 34 is also used to drain inflation fluid from first inflatable portion 28 and second inflatable portion 32 when it is desired to deflate the balloon. First and second inflatable portions are initially deflated when directing the stent delivery device to the bifurcation lesion in a patient. In this embodiment, the inflation lumen 34 inflates inflatable portions 28, 32 substantially simultaneously. In an alternative embodiment, branch balloon portions 27 and 30 have separate inflation lumens. In this alternative embodiment inflatable portions 28 and 32 can be inflated simultaneously or sequentially. When sequential inflation is desired, preferably, the first inflatable portion 28 is inflated first, followed by the inflation of the second portion 32.

First main guidewire lumen 22 extends through main vessel branch portion 18 and first inflatable portion 28. Although first guidewire lumen 22 extends through first inflatable portion 28 in the embodiment depicted in FIGS. 1-2, it is distinct from inflation lumen 34 and is not in fluid communication with the interior of balloon 26 as shown. Preferably, the first guidewire lumen 22 extends distally of first inflatable portion 28 and has an open distal end. Alternatively, guidewire lumen 22 can extend through branch portion 30.

In the embodiment depicted in FIGS. 1-2, an optional side sheath 20 is illustrated which does not include an inflatable balloon. However, in alternate embodiments side sheath 20 could include an inflatable portion as discussed in more detail below and in co-pending U.S. patent application Ser. No. 10/644,550 entitled "Stent With A Protruding Branch Portion for Bifurcated Vessels," for example. Side sheath 20 can be exterior to and distinct from inflation lumen 34 and, if so, would not be in fluid communication with the interior of balloon 26 as shown. As shown in the embodiment of FIGS. 1-2, side sheath 20 preferably extends distally of balloon 26, and may include a proximal open end 37 at any point along the length of the stent delivery system and a distal open end 39. Side sheath 20 can be of the type as described in U.S. Pat. No. 6,325,826 to Vardi, et al., for example, and in operation the side sheath 20 can extend through a branch access hole of the stent.

Figure 3:
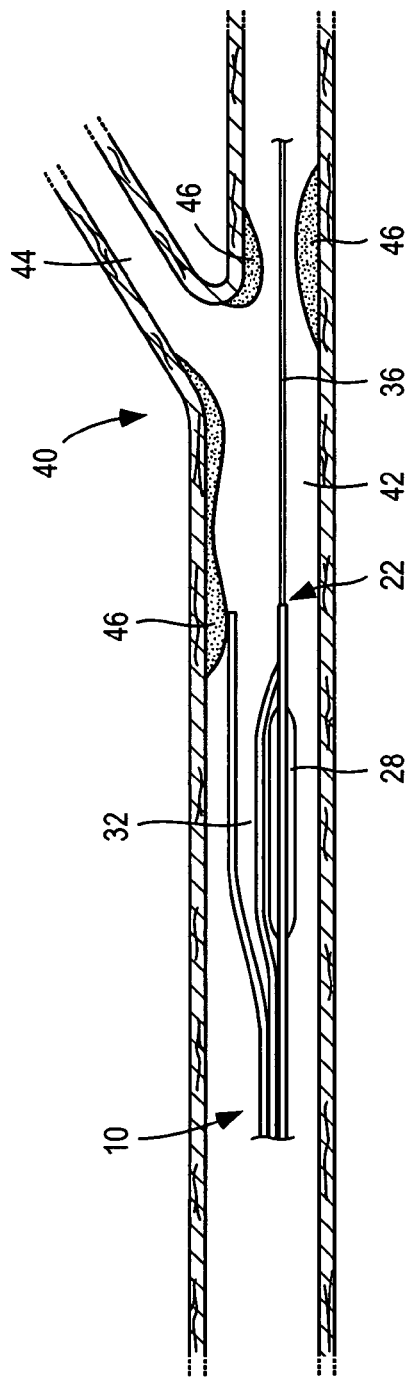
FIG. 3 is a view of the stent delivery system of FIG. 1 in a blood vessel shown approaching a bifurcation in the vessel without a stent mounted thereon in accordance with a method of the present invention.
Figure 4:
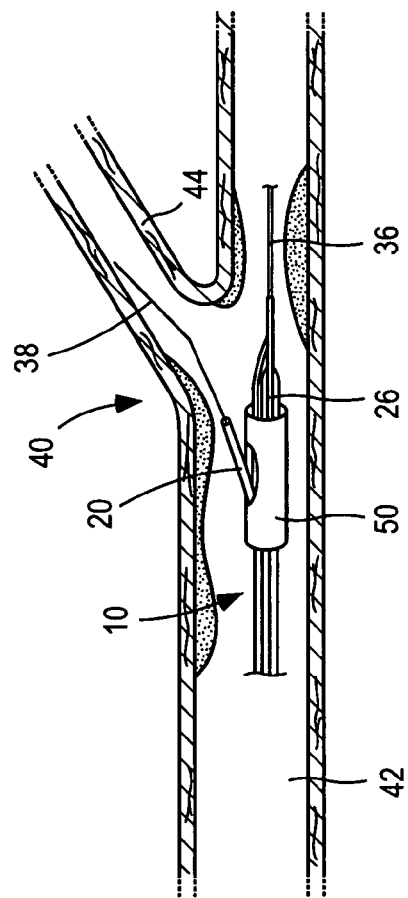
FIG. 4 is a view of the system of FIG. 3, including a stent mounted thereon.

With reference to FIGS. 3-6, an exemplary manner of practicing the invention will now be discussed. Referring to FIGS. 3 and 5, the delivery system is shown in relation to an exemplary body lumen adjacent a blood vessel bifurcation 40 usually comprised of plaque and the delivery system 10 is shown without a stent mounted thereon (FIGS. 3 and 5). FIGS. 4 and 6 show the stent delivery system 10 with a stent 50 mounted thereon.

Bifurcation 40 includes a main vessel 42 and a branch vessel 44. Illustrative obstructions 46 located within bifurcation 40 may span or at least partially obstruct main vessel 42 and a proximal portion branch vessel 44. Generally, stent delivery system 10 may be threaded over a first main guidewire placed in the main vessel to guide the delivery system to the treatment site. More specifically, the proximal end of first guidewire 36 is threaded into the distal open end of the main guidewire lumen 22 and the delivery system is tracked to a position at or near bifurcation 40, as depicted in FIG. 3. Second guidewire 38 (FIG. 5) is then threaded into stent delivery system 10 from the proximal end of the delivery system. More specifically, second guidewire 38 is threaded into the open proximal end 37 of side sheath 20, and may extend therefrom through the open distal end 39 of side sheath 20, as depicted in FIG. 5. Alternatively, second guidewire 38 can be resting dormant on the inside of the side sheath, and when the system is proximal the bifurcation 40, it can be advanced out of side sheath 20 into side branch vessel 44. The systems in accordance with the principles of the invention may be used in over-the-wire or rapid exchange systems, which may include rapid exchange on either or both of the side sheath or main catheter. Rapid exchange is described in one exemplary embodiment in US2003/0181923 to Vardi et al., published Sep. 25, 2003, the entire contents of which are incorporated herein by reference.

In one embodiment, the stent delivery system 10 is positioned near bifurcation 40, and with the distal end 16 (FIG. 1) positioned near side branch vessel 44 (FIGS. 3-6), second guidewire 38 is advanced into side branch vessel 44 from side sheath 20. Then, the first and second inflatable portions of balloon 26 are positioned adjacent the opening of side branch vessel 44 such that auxiliary inflatable side portion 32 of bifurcated balloon 26 is aligned with side branch vessel. In one exemplary embodiment, alignment may be achieved using markers, as described in U.S. Pat. No. 6,692,483 to Vardi, et al., the entire contents of which is incorporated herein by reference. Second guidewire 38 remains in side branch sheath 20, and the distal end 16 of system 10 remains in main vessel 42. First guidewire 36 remains within first guidewire lumen 22, and may be further advanced and positioned in main branch vessel 42.

Once the system is properly positioned, pressurized fluid is supplied to first and second inflatable portions 28 and 32, respectively, of balloon 26 to dilate the body lumen and expand a stent mounted thereon (FIG. 6). Preferably, the inflatable portion 28 expands the main body of the stent and inflatable portion 32 expands the side (opening) and expandable branch structure of the stent, as discussed in more detail with reference to FIG. 6. After inflatable portions 28 and 32 have been inflated as described above, balloon 26 is deflated by draining the inflation fluid via inflation lumen 34. This allows the inflatable portions 28 and 32 to collapse in preparation for withdrawal of the assembly from vessel 42.

Referring now to FIGS. 4 and 6, one preferred embodiment is shown with stent delivery system 10 and an exemplary stent 50 mounted on the exterior of distal end 16 of the stent delivery system. Stent 50 includes an extendible branch portion 52 configured to extend into a branch vessel as discussed, for example, in U.S. Pat. No. 6,210,429 and in co-pending U.S. application Ser. No. 10/644,550, entitled "Stent with Protruding Branch Portion for Bifurcated Vessels". The second inflatable portion 32 may be configured and positioned to deploy the outwardly expanding stent elements or branch portion 52 and may be positioned adjacent to the branch portion 52, or into a side branch access opening in the stent. As shown in FIG. 6, when first and second inflatable portions 28 and 32 are expanded, they simultaneously or sequentially, depending upon the configuration of the inflation lumen, cause the stent 50 to expand in the main vessel 42 and the branch portion 52 of stent 50 to be pushed or extended into the branch vessel 44. Upon inflation of the balloon 26, the second inflatable portion 32 expands and extends the branch portion 52 toward the branch vessel to open and support the entrance or ostium of the side branch artery. This would occur simultaneously when the balloons share a common inflation lumen but could be sequentially if separate inflation lumens are used. Although a bifurcated balloon is depicted, as shown, more than two inflatable portions or more than two balloons may be utilized with the present invention, or a single balloon can be used herein as discussed with reference to FIGS. 12-14.

Further, although the second inflatable portion 32 of the embodiment illustrated in FIGS. 1-6 are shown as being centrally located on the second branch portion 30, it should be noted that the inflatable portion 32 may be located at any desired position along the length of the second branch portion 30. For example, once associated with a stent, it preferably can be placed such that it corresponds to the location along the middle ⅓ of the stent, or, adjacent the extendible branch structure.

As illustrated, for example, in FIGS. 5 and 6, the first and second branch portions 27 and 30 have a longitudinal axis A. The longitudinal axes are substantially parallel with each other. The term "substantially parallel" is intended to encompass deviations from a purely parallel relationship which may be caused by flexure of the branch portions 27 and 30, or other components, experienced during insertion, travel, and deployment within a body lumen.

Figure 7:
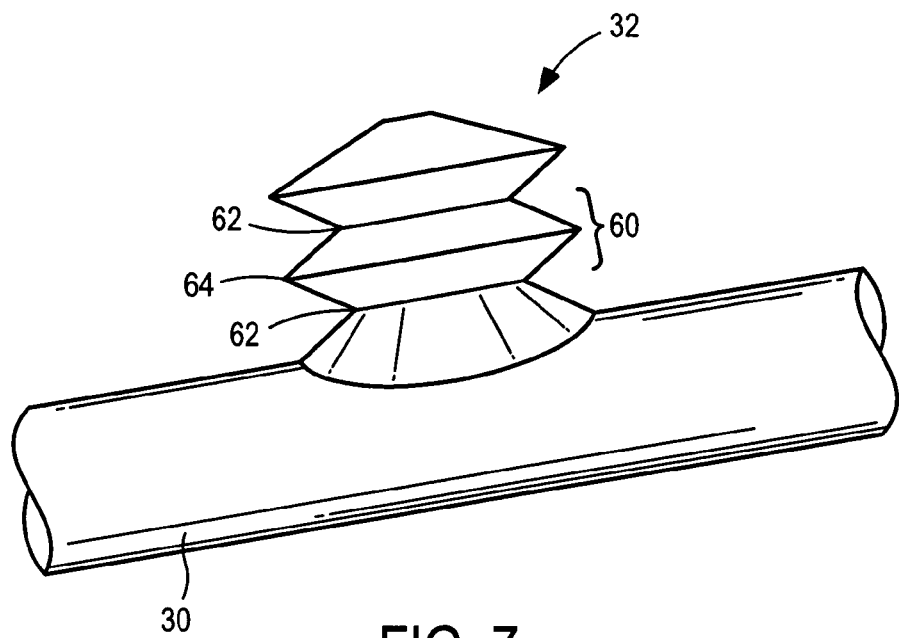
FIG. 7 is an enlarged side view of an accordion balloon of the stent delivery system of FIG. 1.

Referring now to FIG. 7, the accordion feature will now be described in more detail with reference to an exemplary embodiment. FIG. 7 is an enlarged view of inflatable side portion 32 of bifurcated balloon 26 as depicted in FIGS. 1-6. The inflatable side portion 32 is constructed to extend laterally outwardly from a longitudinal axis of the system and into the branch vessel. As shown, the inflatable side portion 32 has a generally "accordion" shape in that it includes a series of fluidly connected cells 60. The accordion cells 60 preferably have a broad central portion 64 which tapers to narrower end portions 62. Thus, when viewed in profile, the cells 60 typically have a "flattened" hexagon shape when inflated. However, the shape of the profile is not critical. For example, the profile of the cells 60 may have a more rounded shape. Further, the accordion structure 33 may be constructed so that upon maximum inflation, the individual cells 60 merge, resulting in a generally tubular structure. When deflated, the cells collapse into a low profile configuration as discussed in more detail in the following.

The individual cells 60 are fluidly connected via the narrow end portions 62. Thus, fluid entering the first cell 60 of the inflatable side portion 32 of the balloon 26 passes to successive cells 60 in the series of cells 60 comprising the inflatable side portion 32, creating an axis of primary inflation from the first cell 60 to the final cell 60. In this manner, the inflatable side portion 32 can expand to a greater extent along the axis of primary inflation than in the radial direction perpendicular to the axis of primary inflation. As such in the unexpanded condition, the balloon is substantially flat, e.g., a flat flexible disc shape, and in the expanded configuration the balloon length significantly increases along the axis of primary inflation. By comparison, for example, the main balloon 28 has a relatively fixed longitudinal length that remains substantially unchanged upon expansion.

When viewed along the axis of primary inflation, the cells 60 are preferably round. However, any shape may be used. For example, the cells 60 may be, but are not limited to being, elliptical, square, hexagonal or octagonal. Further, successive cells 60 need not be the same size. For example, successive cells 60 may decrease or increase in size from the preceding cell 60, resulting in a tapered inflatable side portion 32.

The components of the auxiliary inflatable side portion 32 may be sized appropriately, as will be readily apparent to those skilled in the art. The accordion structure 33 can be provided with a suitable inflated cell diameter and connector diameter. The diameters can vary according to various factors known to those skilled in the art. Further, the auxiliary inflatable side portion 32 can comprise any number of cells 35 as determined for the particular application. Additionally, the expansion of the second inflatable portion 32 produces a force and a configuration to deploy a branch portion 52 of a stent 50 into a side branch vessel 44. Accordingly, second inflatable portion 32 may unfold or push out the branch portion 52 of the stent while controlling or limiting the radial expansion as desired.

Branch vessel inflatable portion 32, as discussed above and as shown, includes an embodiment of the accordion feature and other embodiments are shown herein and discussed in the following. The accordion configuration of the inflatable portion 32, however, can include different shapes, sizes and construction in accordance with the principles of the invention. For example, the accordion feature can be combined with the embodiments disclosed in U.S. Provisional Patent Application Ser. No. 60/518,870, entitled "Stent Delivery Systems." Also, the accordion principles discussed above with reference to FIGS. 1-7 apply to the other embodiments discussed herein.

Figure 8:
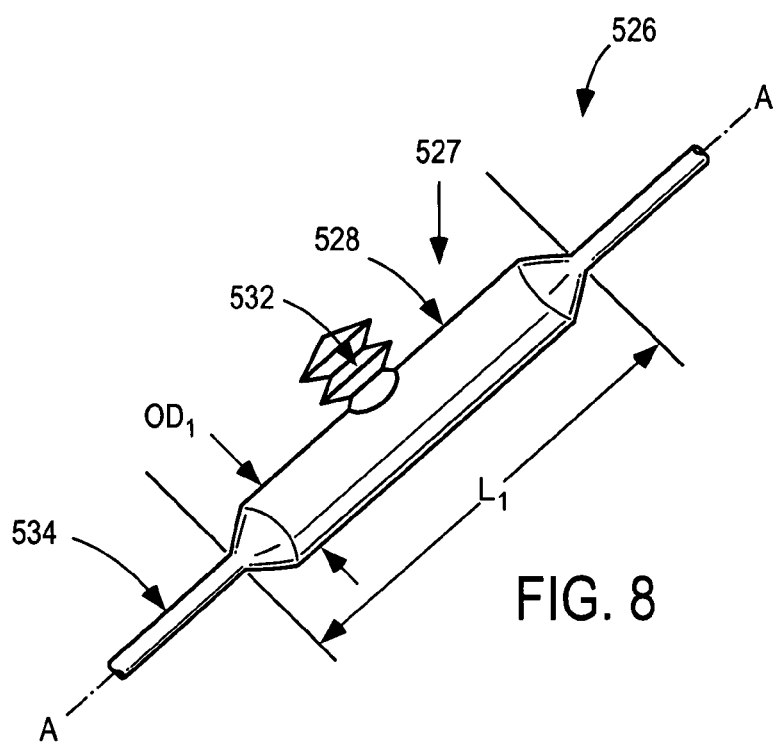
FIG. 8 is a perspective view of a portion of a stent delivery system constructed according to an alternative embodiment of the present invention.

FIG. 8 illustrates an alternative embodiment of the present invention also for use in the treatment of branch arteries, including alone or, for example, by incorporation into stent delivery systems of the type previously described. The balloon depicted in the embodiment of FIG. 8 can be referred to as a "herniated" accordion balloon configuration that functions in a manner similar to the embodiments described above. The herniated accordion balloon configuration is characterized by having a generally cylindrical shape in an unexpanded configuration, and a generally cylindrical shape with a generally accordion shaped appendage that inflates outwardly relative to the longitudinal axis of the balloon toward the branch artery in an expanded state or configuration. This protrusion can be referred to as a herniation, bulge, protrusion, or extension, for example. The particular shape, size, and configuration of the balloon and the accordion herniations illustrated herein are exemplary, and may be modified from that explicitly shown and described. The expandable herniation, bulge, protrusion, or extension can be expandable towards the entrance of side branch (see, e.g., 44, FIG. 3) over a suitable dimension, such as 1-4 mm.

The embodiment of the balloon depicted in FIG. 8 can be utilized in a manner similar to that which has been described in connection with previously illustrated embodiments (see, e.g., FIGS. 1-7). With regard to the embodiment depicted in FIG. 8, it should be understood that the herniated accordion balloon construction depicted herein can be used alone or can be substituted for the entire bifurcated balloon (e.g. 26, FIGS. 1-7) or a portion of the bifurcated balloon (e.g., 32) with certain modifications, as needed, in accordance with the principles of the invention.

An exemplary embodiment of a herniated accordion balloon catheter 526 is illustrated in FIG. 8. In the illustrated embodiment, the herniated balloon catheter 526 comprises a balloon 527 having an elongated inflatable portion 528 and an accordion herniation, bulge, protrusion, or extension 532.

In the embodiment of FIG. 8 the balloon catheter 526 further includes a lumen 534 which can serve to communicate pressure for inflation of the balloon 527, and provide a passageway for a guide wire, etc.

The particular configuration and dimensions of the balloon 527 can vary according to a number of factors. For purposes of illustration only, certain suitable, but non-limiting, dimensions of various components of the balloon 527 will now be described. The balloon 527 can be provided with a length dimension $L_1$ which is about 4-100 mm. The balloon can be provided with an outside diameter $OD_1$ which is on the order of about 1-10 mm.

Although the accordion herniation 532, of the embodiment illustrated in FIG. 8 are shown as being centrally located on the herniated balloon 527, it should be noted that the herniation 532 maybe located at any desired position along the length of the balloon. For example, once associated with a stent, it can preferably be placed such that it corresponds to the location along the middle ⅓ of the stent and/or adjacent the extendible branch structure of the stent.

The balloon 527 can be constructed of any suitable material such as those previously disclosed herein. In addition, the balloon 527, as well as any other embodiments described herein, can be constructed of a composite material. Suitable materials include a combination of elastomeric and semi to non-compliant materials such as: urethane; silicone; nylon; latex; (elastomeric) polyethylene hytrel pebax polyaryletherthketone; polyoxymethylene; polyamide; polyester thermoplastic polyetheretherkatone; and polypropylene (semi non-compliant). The balloon 526, can be also be constructed by combining the above-disclosed materials with woven textile materials such as Kevlar, silk, cotton, wool, etc. This can be accomplished by winding or weaving a textile material onto a rod that has the shape of the desired accordion herniated balloon. The polymer component of the composite is then extruded or dip-coated over the rod. This composite structure is then cured, heat set, or adhesively fused together. The rod is then removed and the remaining shape comprises the accordion herniated balloon 527. Alternatively, this can be accomplished by combining the above-described materials with woven material only on the main balloon portion and not on the accordion balloon portion, whereby upon application, by whatever process, the elastomeric or polyurethane, for example, alone forms the accordion balloon portion.

The accordion herniation 532, can be provided by adding an appendage to a conventional balloon by using a molded collar or adhesively attaching an object to the surface of the balloon, or by using a mound of adhesive to create the herniation.

The balloon 527 can be constructed by molding three small balloons and attaching them in tandem, the central balloon comprising the desired shape of the accordion herniation. These balloons would share a common inflation port. When the balloons are inflated, the center balloon expands in the desired manner to form the accordion herniation.

Figure 9:
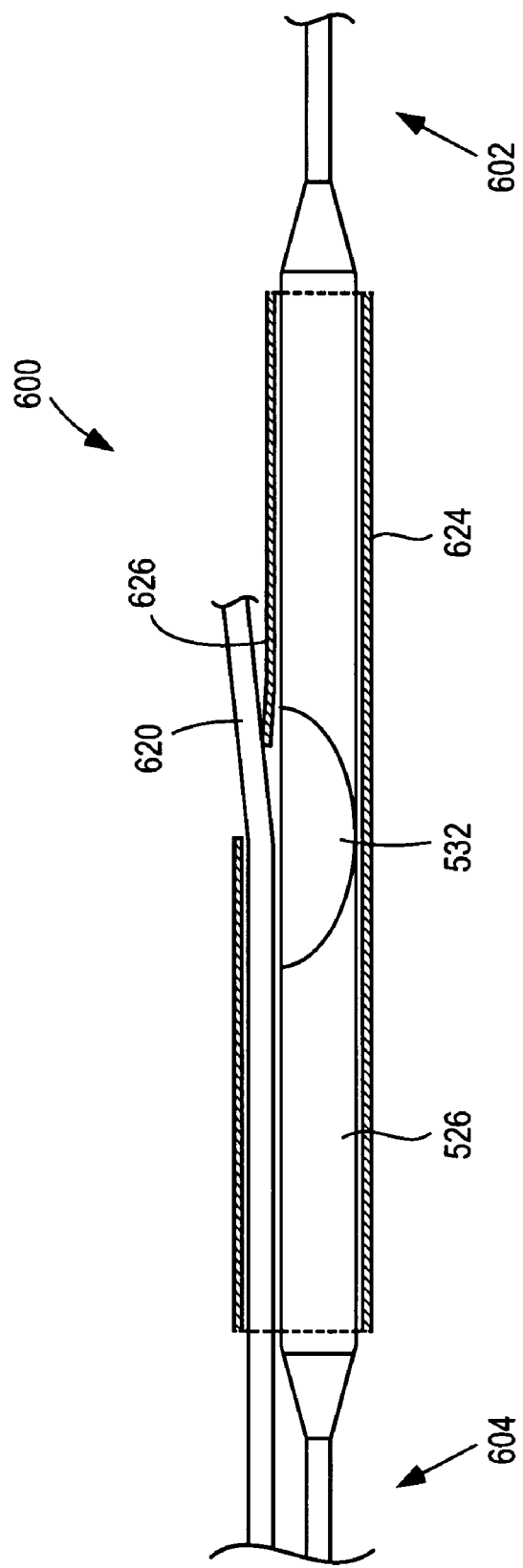
FIG. 9 is a side view of the stent delivery system of FIG. 8 with a cut-away view of a stent mounted thereon in an unexpanded condition.
Figure 10:
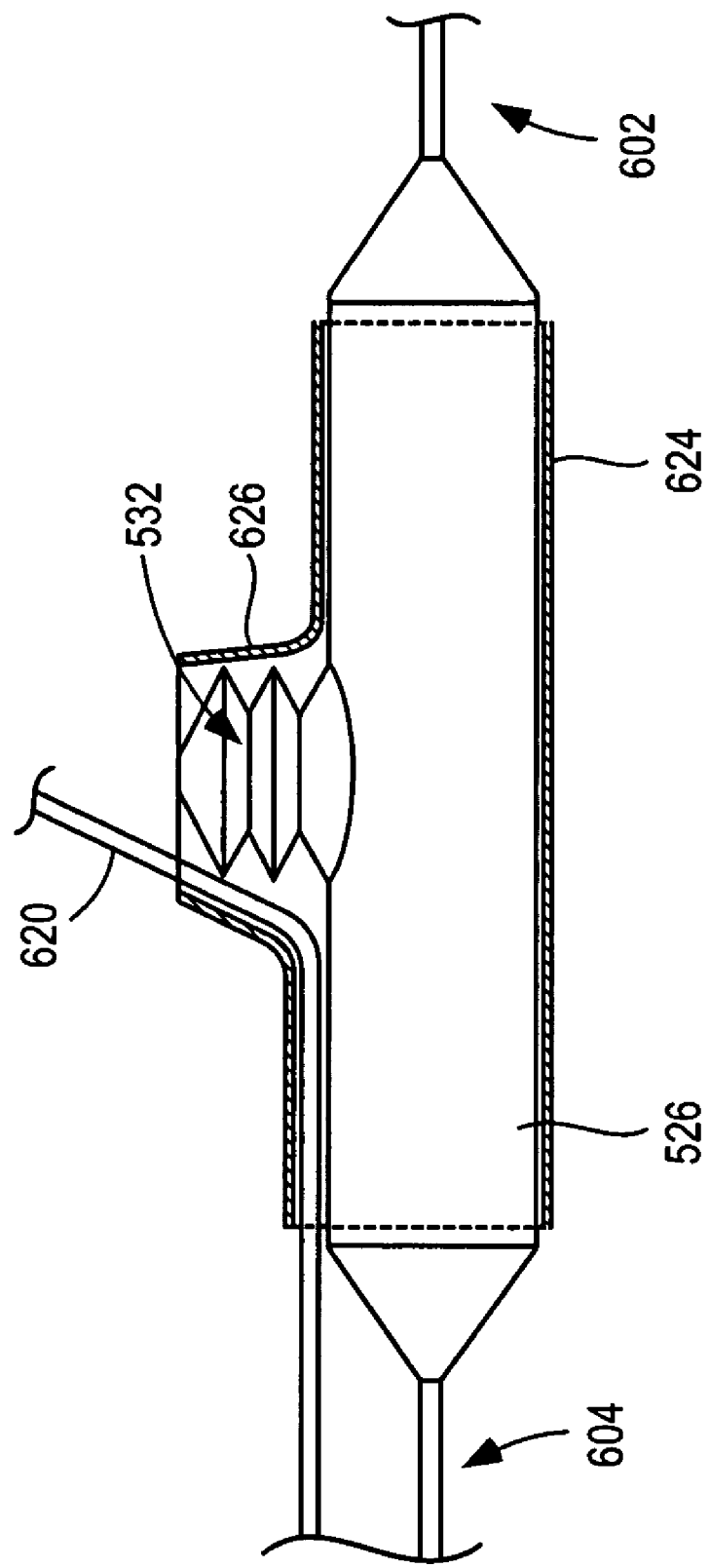
FIG. 10 is a side view of the stent delivery system of FIG. 9 with a cut-away view of a stent mounted thereon in an expanded condition.

FIG. 9 shows balloon 527 in a stent delivery system 600, of which only the distal end portion is shown. System 600 is shown in an unexpanded condition. The distal end is shown at 602 and the proximal end at 604. The system 600 generally includes balloon 526, side sheath 620 and bifurcated stent 624, of the type discussed above. The stent is depicted generally and without detail for illustration. Side sheath 620 extends through a side branch access opening in stent 624. In this figure, the unexpanded accordion herniation is shown at reference numeral 532. When unexpanded or collapsed, the accordion herniation 532 is a substantially flat configuration, for example, a flat flexible disc shape. As illustrated, the unexpanded accordion herniation 532 is disposed against the side of balloon 526, such as by folding. However, it is not necessary for the unexpanded accordion herniation 532 to be folded in this manner. For example, the unexpanded accordion herniation 532 may be folded entirely on top of balloon 527. In fact, any folding technique may be used as long as the herniation 532 is capable of being expanded and, in particular, expanded to deploy branch portion 626. FIG. 10 shows system 600 in an expanded condition with accordion herniation 532 expanded to deploy branch portion 626 of stent 624 outwardly into a branch vessel (not shown).

As illustrated, the accordion herniation 532 in this embodiment and the second inflatable portion 32 in the previous embodiment are shown to expand in a direction substantially perpendicular to the longitudinal axis of the elongate inflatable potions 528, 28 of those respective embodiments. However, the accordion herniation 532 and the second inflatable portion 32 may be fabricated to expand at any angle relative to the elongate inflatable potions 528, 28 as required by the particular configuration of the vessels of the bifurcation to be treated. Additionally, in these embodiments the axis of inflation of the accordion structure 33 is generally at an angle to the axis of the inflation lumen supplying air to the accordion structure 33.

Figure 11:
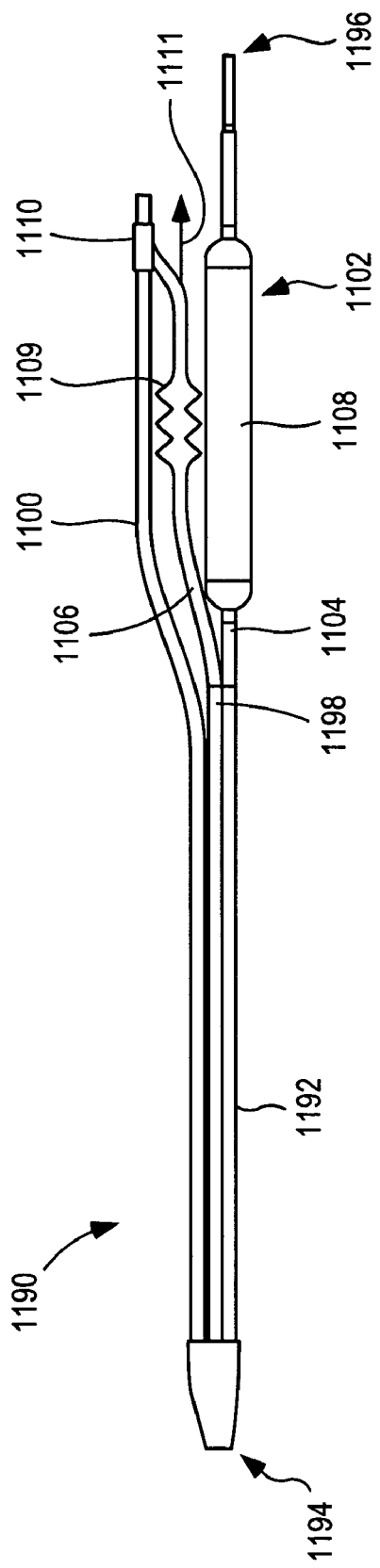
FIG. 11 is side view of a stent delivery system according to another embodiment of the invention.
Figure 12:
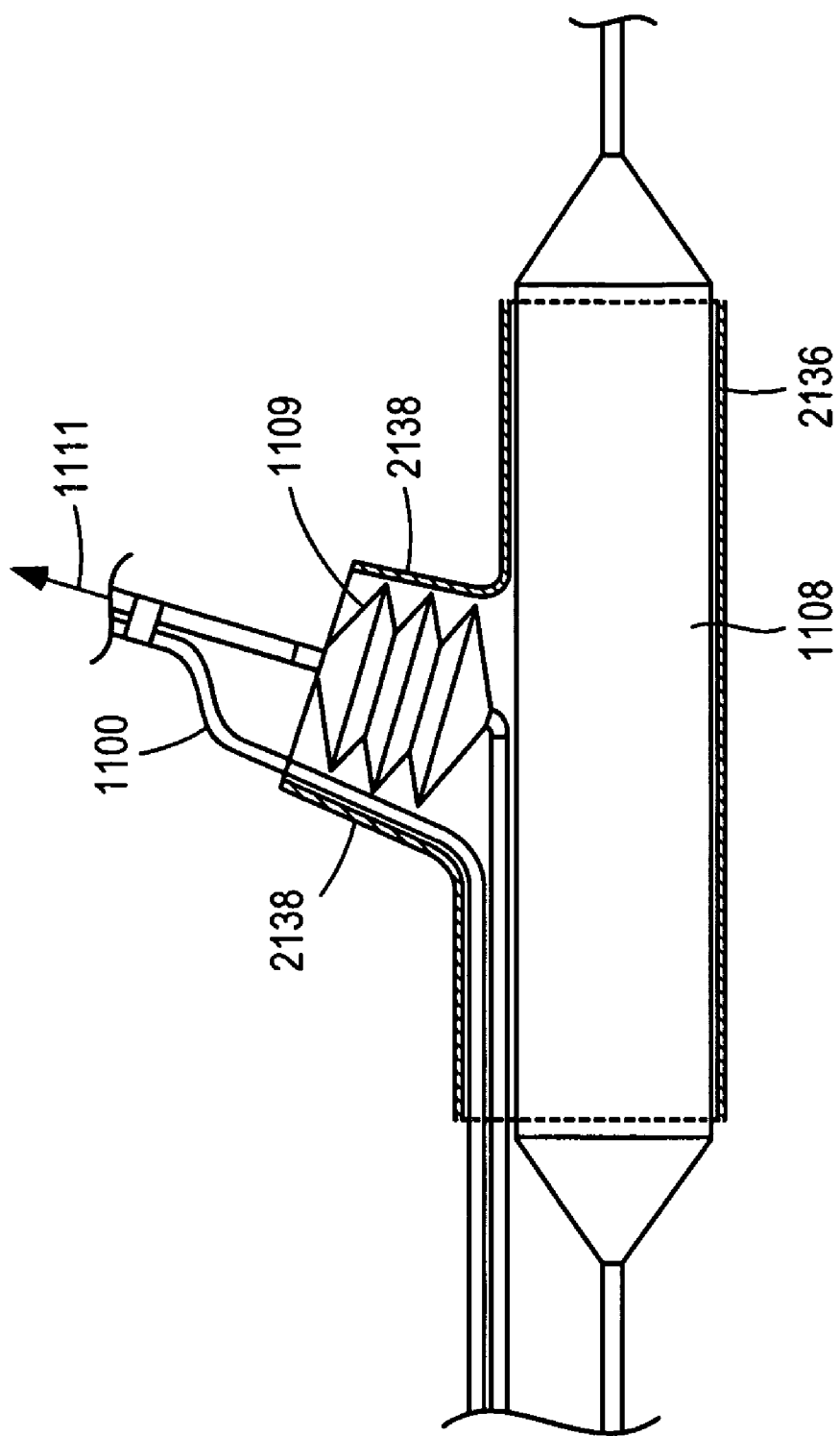
FIG. 12 is a side view of the stent delivery system of FIG. 11 with a partial cut-away view of a stent mounted thereon in an expanded condition.

Referring now to FIGS. 11-12, an alternative embodiment of a stent delivery system 1190 is shown. Stent delivery system 1190 comprises an elongate main catheter shaft 1192 extending from a proximal end 1194 to a distal end 1196. Distal end 1196 can include a bifurcated structure with two branch portions, a main vessel branch portion 1198 and a side branch sheath 1100. Main vessel branch portion 1198 itself can include two branches, a first branch 1104 which can include a balloon 1102 and an accordion branch portion 1106. Balloon 1102 can include an elongate inflatable portion 1108 that extends along first branch portion 1104 of main vessel branch portion 1198.

Accordion branch portion 1106 can extend between main vessel branch portion 1198 to about the distal end of side branch sheath 1100. Accordion branch portion 1106 can include a generally axially inflatable portion 1109, in particular, an accordion balloon. In general, inflatable portion 1109 is configured and designed such that upon inflation it expands or elongates along an axis, for example, its longitudinal axis 1111. In a preferred embodiment of the invention, the distal end of axially inflatable portion 1109 is slidably attached to side sheath 1100 while the proximal end can be secured to main vessel branch portion 1198. Portion 1109 can be slidably attached by any structure in accordance with the principles of the invention, including, for example, a flexible tube.

In one method of slidable attachment, the distal end of axially inflatable portion 1109 may be fixedly attached to a tubular member 1110 that is slidably received on the exterior of side sheath 1100. In a preferred embodiment, axially inflatable portion 1109 is generally shaped and/or folded similar to an accordion and upon inflation, inflatable portion 1109 unfolds or expands in an axial direction, along its longitudinal axis 1111. In this manner, the distal tip of inflatable portion 1109 slides in the distal direction along side sheath 1100.

In operation, when a stent 2136 is mounted on the delivery system 1190 and delivered to a vessel bifurcation, outwardly deployable elements or branch portions 2138 of the stent 2136 may be advantageously deployed by axially inflatable portion 1109 (FIG. 12). Inflatable portion 1109 is disposed within stent 2136 in the unexpanded configuration and is expandable along its axis, e.g., its longitudinal axis, into the branch vessel. Because inflatable portion 1109 slides along side sheath 1100 in the distal direction, an axial force is created in the direction of side sheath 1100 that may more efficiently deploy a branch portion 2138 of a stent 2136 into a side branch vessel. The axial force created may unfold or push out the branch portion 2138 of the stent while controlling or limiting the radial expansion as desired. As a result, a stent 2136 may be designed having a branch portion that can more effectively treat lesions in a side branch vessel. For example, in some stent 2136 designs the extendible branch portion 2138 of the stent 2136 may be extended further into the branch using this delivery system configuration.

Figure 13:
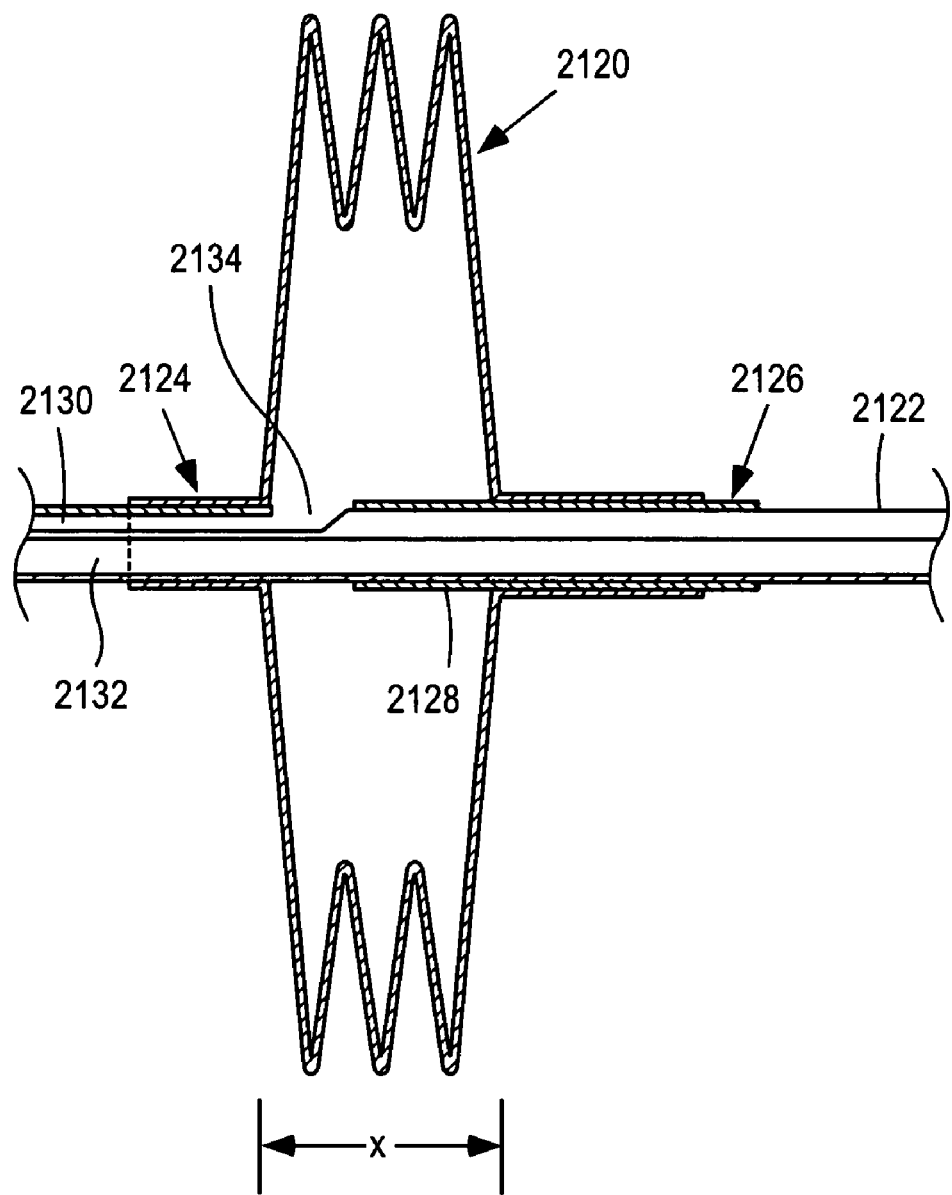
FIG. 13 is a partial cut-away view of another embodiment of a stent delivery system with a slidable accordion balloon partially expanded.
Figure 14A:
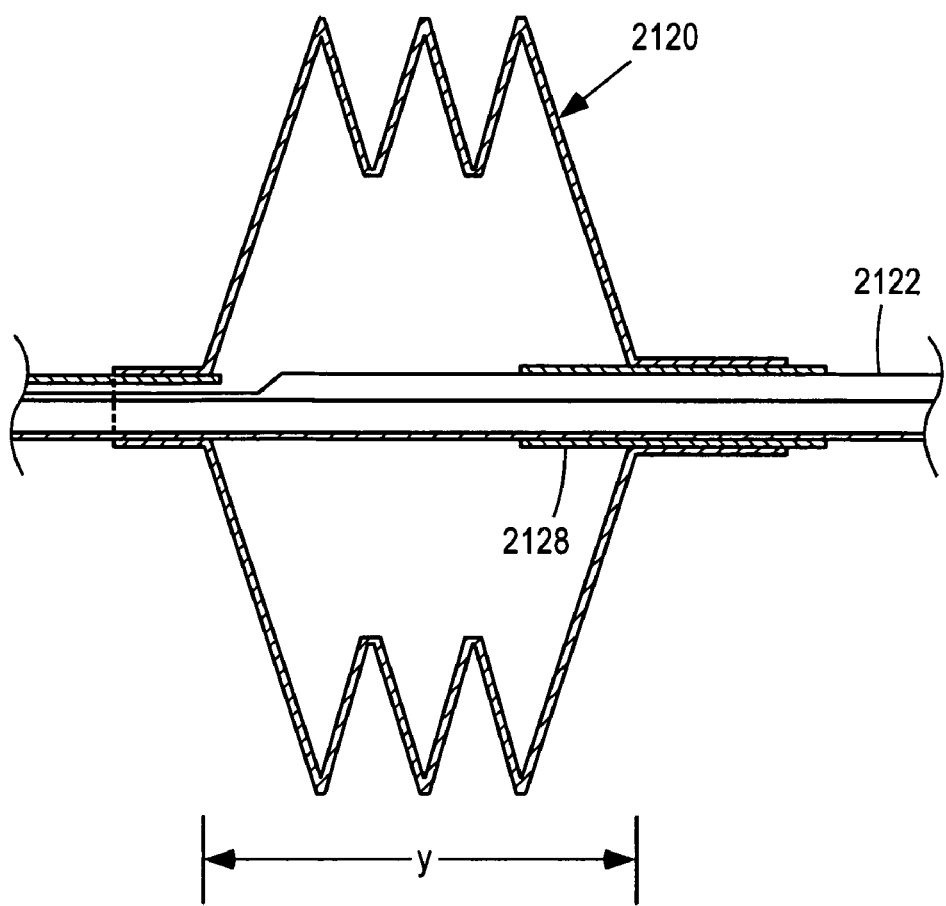
FIG. 14A is a partial cut-away view of the system shown in FIG. 13 with the accordion balloon further partially expanded.
Figure 14B:
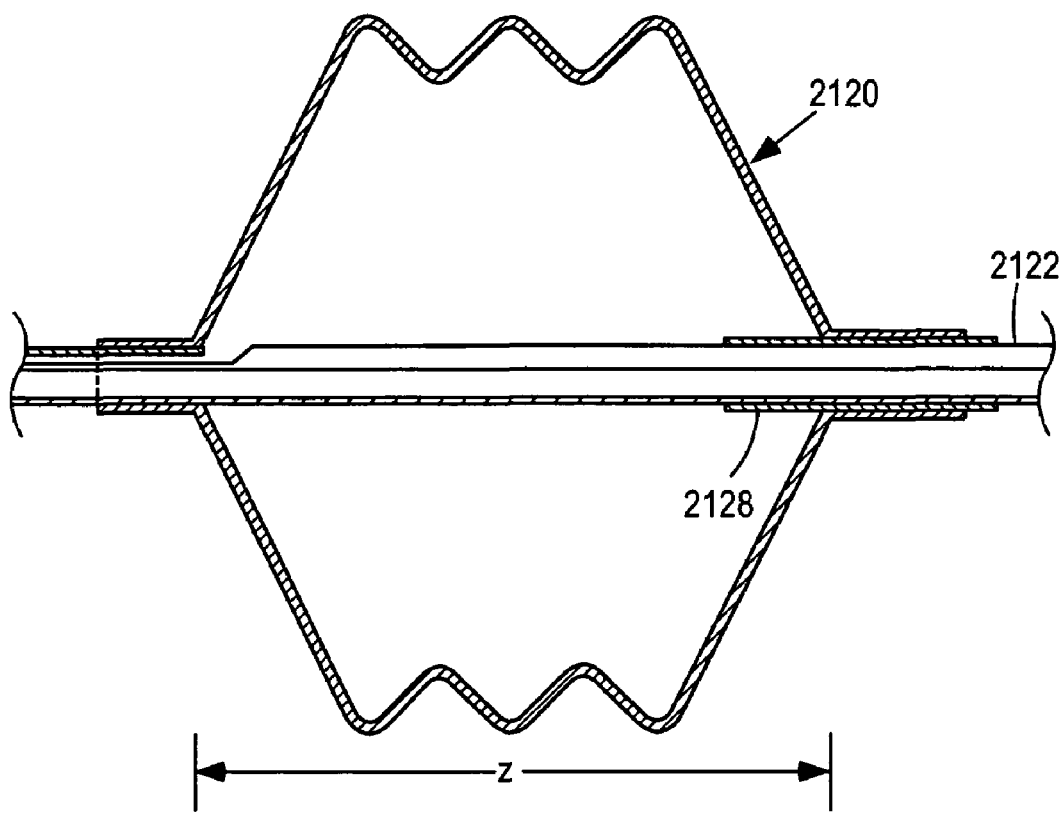
FIG. 14B is a partial cut-away view of the system shown in FIG. 14A with the accordion balloon further expanded.

Referring to FIGS. 13, 14A and 14B, an alternative embodiment of an accordion or axially inflatable balloon 2120 is shown. Balloon 2120 extends coaxially along a catheter or sheath 2122. Sheath 2122 includes an inflation lumen 2130 for inflating balloon 2120 and a guidewire lumen 2132 for receiving a guidewire. Inflation lumen 2130 is in fluid communication with balloon 2120 through balloon intake 2134. Proximal end 2124 of balloon 2120 is fixedly attached to sheath 2122 and distal end 2126 of balloon 2120 is fixedly attached to a tubular member 2128, which is slidably received on the exterior of sheath 2122. Tubular member 2128 can be a flexible tube. Tubular member 2128 preferably has a length sufficient to be attached to the balloon material and sufficient to extend into the balloon 2120 to form a fluid-tight seal when balloon 2120 is inflated. In particular, tubular member 2128 is constructed so that, upon inflation, it is slidable along sheath 2122, yet the end of sheath 2122 that is inside the balloon, when inflated, is pressed against sheath 2122 in an amount sufficient to create a fluid-tight seal. In operation, upon inflation, distal end 2126 is slidable along sheath 2122, by way of tubular member 2128 to expand balloon 2120 from x amount of expansion as shown in FIG. 13, further to y amount of expansion as shown in FIG. 14A, even further to z amount of expansion as shown in FIG. 14B where x<y<z. In an alternative embodiment, not shown, both proximal and distal ends 2124, 2126 could be fixedly secured to a sheath extending from the distal end and a sheath extending from the proximal end in accordance with the principles of the invention.

Figure 15:
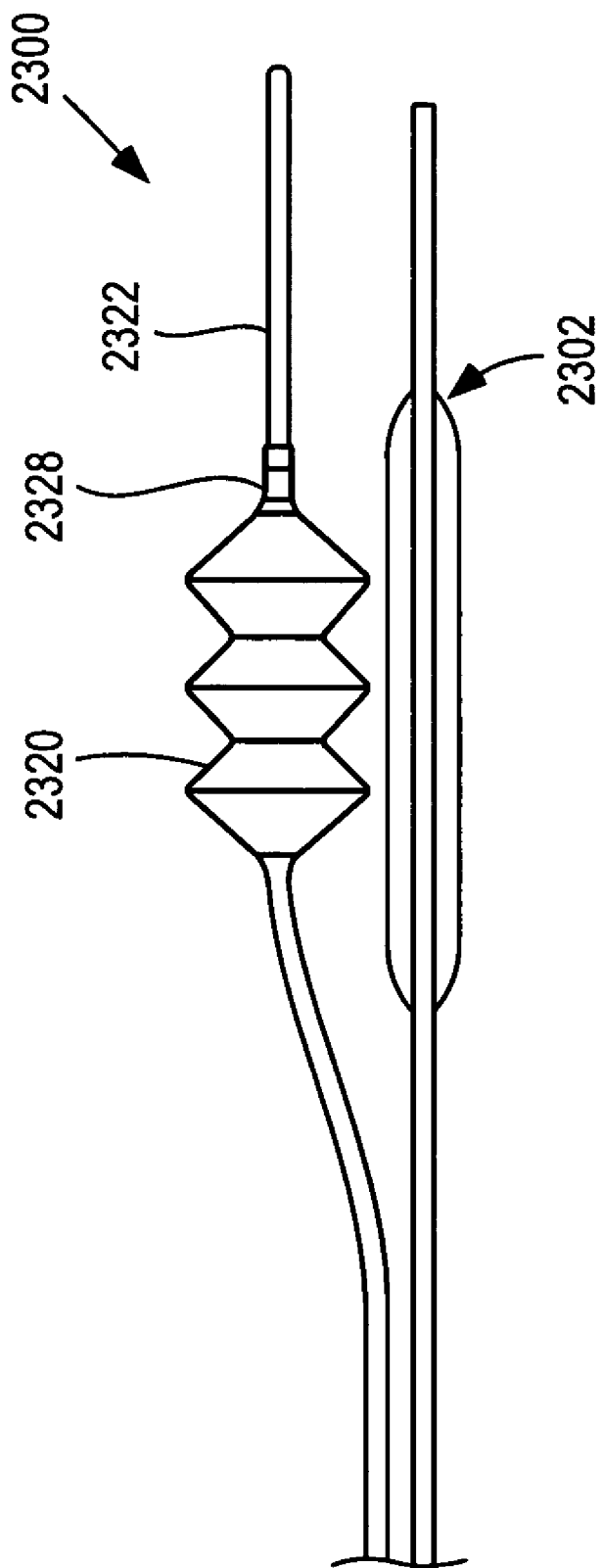
FIG. 15 is a side view of a stent delivery system according to another embodiment of the invention in an expanded condition.
Figure 16:
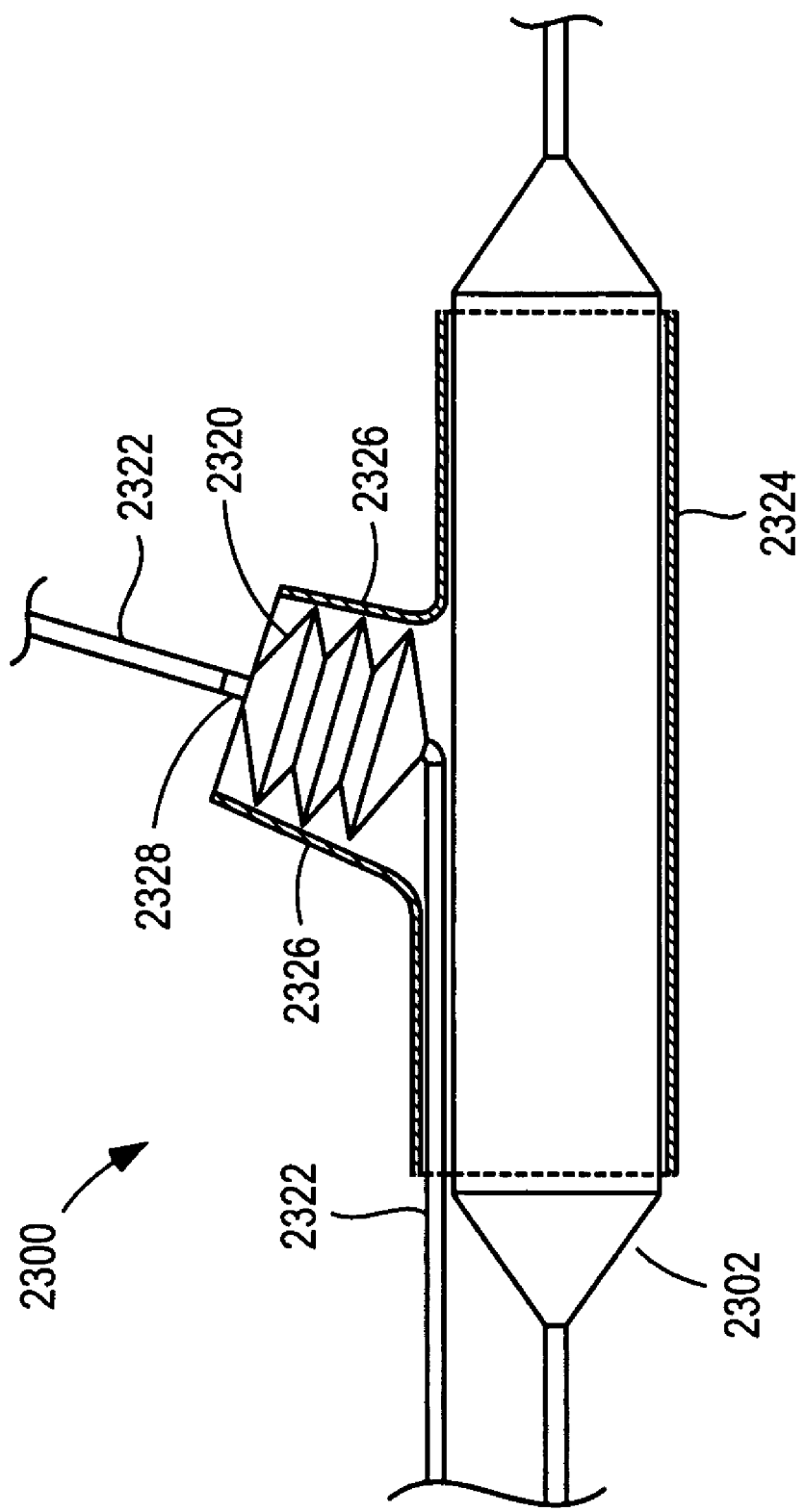
FIG. 16 is side view of the stent delivery system of FIG. 15 with a partial cut-away view of a stent in an expanded condition.
Figure 17:
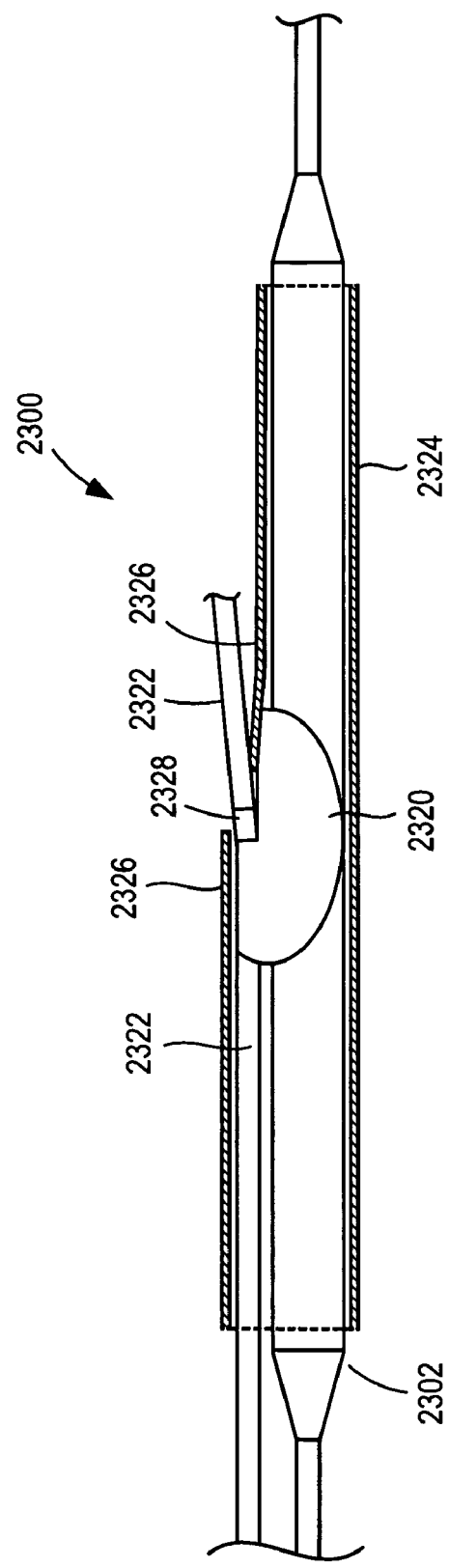
FIG. 17 is a side view of the stent delivery system of FIG. 15 with a partial cut-away view of a stent in an unexpanded condition.

The embodiment of FIGS. 13, 14A and 14B can be used alone or in combination with other embodiments disclosed herein. For example, sheath 2122 (FIGS. 13, 14A and 14B) may be part of a stent delivery system. As shown in FIGS. 15-17, stent delivery system 2300 can include a side sheath 2322, of the type described with reference to FIGS. 13, 14A and 14B, and main balloon catheter 2302. Side sheath 2322 includes accordion balloon 2320 with tubular member 2328 as discussed above. FIG. 16 shows a stent 2324 mounted on system 2300 in an expanded condition, while FIG. 17 shows a stent 2324 mounted on system 2300 in an unexpanded condition. When stent 2324 having a branch portion 2326 is mounted on the delivery system and delivered to a vessel bifurcation, sheath 2322 may extend through a side branch access hole of the stent 2324 with balloon 2320 positioned adjacent an interior of the branch portion. As in the embodiment illustrated in FIGS. 13, 14A and 14B, the accordion balloon 2320 may be folded in any manner that allows for deployment of the branch portion 2326 of stent 2324. Upon inflation, balloon 2320 expands axially by tubular member 2328 sliding distally along sheath 2322 in the distal direction creating an axial force along the axis of the side sheath. The axial force created can expand or push out the branch portion 2326 of the stent 2324 into the branch vessel a sufficient distance into the branch vessel and without unnecessarily expanding the branch portion 2326 radially. As a result, a stent 2324 has a branch portion 2326 that can more effectively be used to treat lesions in a side branch vessel. For example, in some stent designs the extendible branch portion 2326 of the stent 2324 may be extended further into the branch using this delivery system configuration.

In an alternative embodiment, the embodiments of FIGS. 11-17 can associate the accordion balloon with side sheath so that upon expansion the accordion balloon follows the side sheath into the side branch vessel.

Although the invention has been described for use with a single accordion balloon, the use of one or more accordion balloons is contemplated as discussed, for example, in co-pending U.S. patent application Ser. No. 10/834,066, entitled "Catheter Balloon Systems and Methods."

Figure 18:
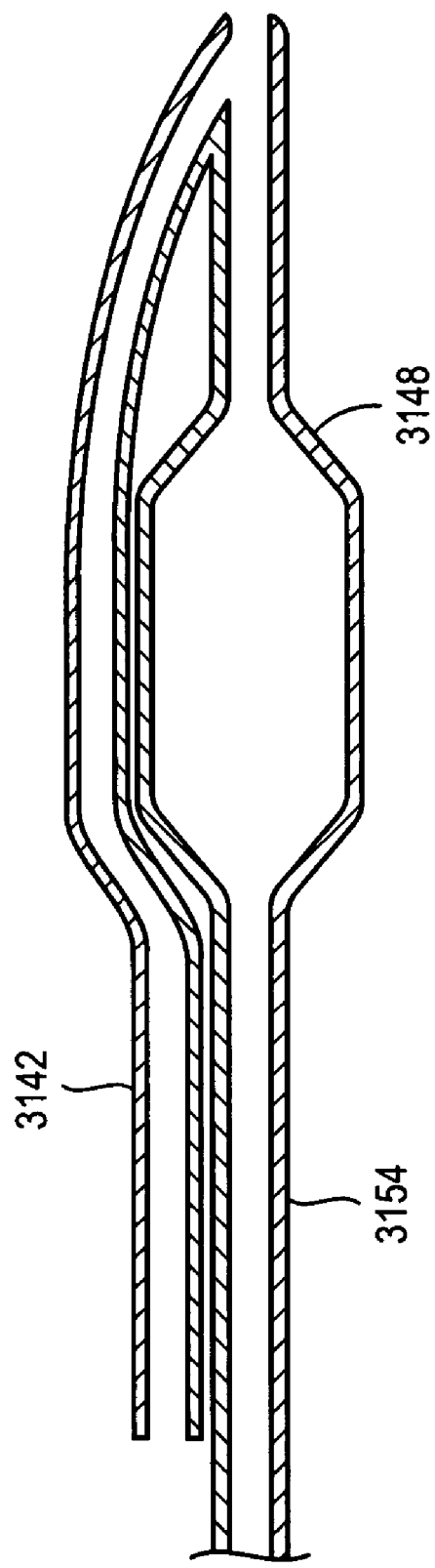
FIG. 18 is a cross-sectional view an embodiment of a delivery system in accordance with the present invention.

In an alternative embodiment, shown in FIG. 18, a first guidewire lumen 3142 may not pass through the interior of first inflatable portion 3148. For example, the lumen may be affixed to the exterior of the balloon, or the balloon may be formed with a plurality of folds through which the guidewire passes. Or the guidewire (not shown) may pass through the folds of the balloon. In this embodiment, guidewire lumen 3142 is separate from the inflation lumen 3154. In a preferred embodiment, guidewire lumen 3142 may have an abbreviated or shorter length as compared to the inflation lumen 3154 thereby providing less lumen for a guidewire to pass through. The distal end of lumens 3142 and 3154 are preferably attached together at the very distal tip of the delivery system, such as by bonding, and the proximal end of the guidewire lumen is connected to the inflation lumen. Thus, this stent delivery embodiment is neither an "over the wire" system (the guidewire lumen does not stay inside the inflation lumen through the entire length of the delivery system). Nonetheless, the abbreviated or shorter length of guidewire lumen 3142 as compared to the inflation lumen 3154 allows, for example, rapid insertion and removal of a guidewire therethrough. This feature can be used on a delivery system regardless of the number of the balloons used, or whether the delivery system utilizes a side sheath. For example, this could be used alone or in combination with other embodiments described herein.

While the invention has been described in conjunction with specific embodiments and examples thereof, it is evident that many alternatives, modifications and variations will be apparent to those skilled in the art upon reading the present disclosure. Accordingly, it is intended to embrace all such alternatives, modifications and variations that fall within the spirit and broad scope of the appended claims. Furthermore, features of each embodiment can be used in whole or in part in other embodiments.

What is claimed is:

1. A catheter assembly for use in bifurcated vessels, comprising:

an elongated catheter body having a proximal end and a distal end; and a balloon arrangement associated with the distal end of the balloon catheter, the balloon arrangement including a main vessel balloon for treating a main vessel of the bifurcation, and a branch vessel balloon for treating a branch vessel of the bifurcation, wherein the branch vessel balloon comprises a plurality of fluidly connected cells connected in series, the series defining an axis of primary inflation; and wherein when the branch vessel balloon is expanded, expansion along the axis of primary inflation is greater than expansion in a radial direction, which is substantially perpendicular to the axis of primary inflation.

2. The catheter assembly of claim 1, wherein successive cells have a different size from the preceding cell in the series.

3. The catheter assembly of claim 1, wherein the cells are adapted to merge into a substantially tubular structure when fully expanded.

* * * * *